United States Patent [19]

Auth

[11] Patent Number: 4,492,231

[45] Date of Patent: Jan. 8, 1985

[54] NON-STICKING ELECTROCAUTERY SYSTEM AND FORCEPS

[76] Inventor: David C. Auth, 4739 Somerset Ave. Southeast, Bellevue, Wash. 98006

[21] Appl. No.: 419,400

[22] Filed: Sep. 17, 1982

[51] Int. Cl.³ .............................................. A61B 17/39
[52] U.S. Cl. ................................................ 128/303.17
[58] Field of Search ....................... 128/303.13, 303.17, 128/303.18

[56] References Cited

U.S. PATENT DOCUMENTS

| | | | |
|---|---|---|---|
| 3,685,518 | 8/1972 | Beuerle et al. | 128/303.17 |
| 3,707,149 | 12/1972 | Hao et al. | 128/303.17 X |
| 3,875,945 | 4/1975 | Friedmen | 128/303.17 |
| 3,902,494 | 9/1975 | Haberlen et al. | 128/303.17 |
| 3,911,241 | 10/1975 | Jarrard | 128/303.17 |
| 4,074,718 | 2/1978 | Morrison, Jr. | 128/303.14 |
| 4,274,413 | 6/1981 | Hahn et al. | 128/303.17 |

FOREIGN PATENT DOCUMENTS 2315286  1/1977  France ............................ 128/303.17

*Primary Examiner*—Lee S. Cohen
*Attorney, Agent, or Firm*—Seed and Berry

[57] ABSTRACT

A non-sticking electrocautery system having bipolar electrocautery forceps connected to an RF signal generator. The forceps includes a pair of electrically conductive arms movable toward and away from each other. The arms terminate in respective jaws which are adapted to grasp tissue to be cauterized. The arms have a thermal conductivity sufficiently high to remove heat from the jaws at a rapid rate. As a result, the surfaces of the jaws that are in contact with the tissue are maintained at a temperature sufficiently low to prevent the tissue from sticking to the jaws. The forceps also include an insulating stop for preventing the jaws from contacting each other. The forceps also include an internal switch which causes the RF signal generator to apply RF power to the forceps when the arms of the forceps are closed. The RF signal from the signal generator has a relatively low voltage so that sparking does not occur from the jaws to either each other or to the tissue. Additionally, the signal generator has an output impedance that delivers a relatively constant power to the tissue as the impedance of the tissue varies.

10 Claims, 4 Drawing Figures

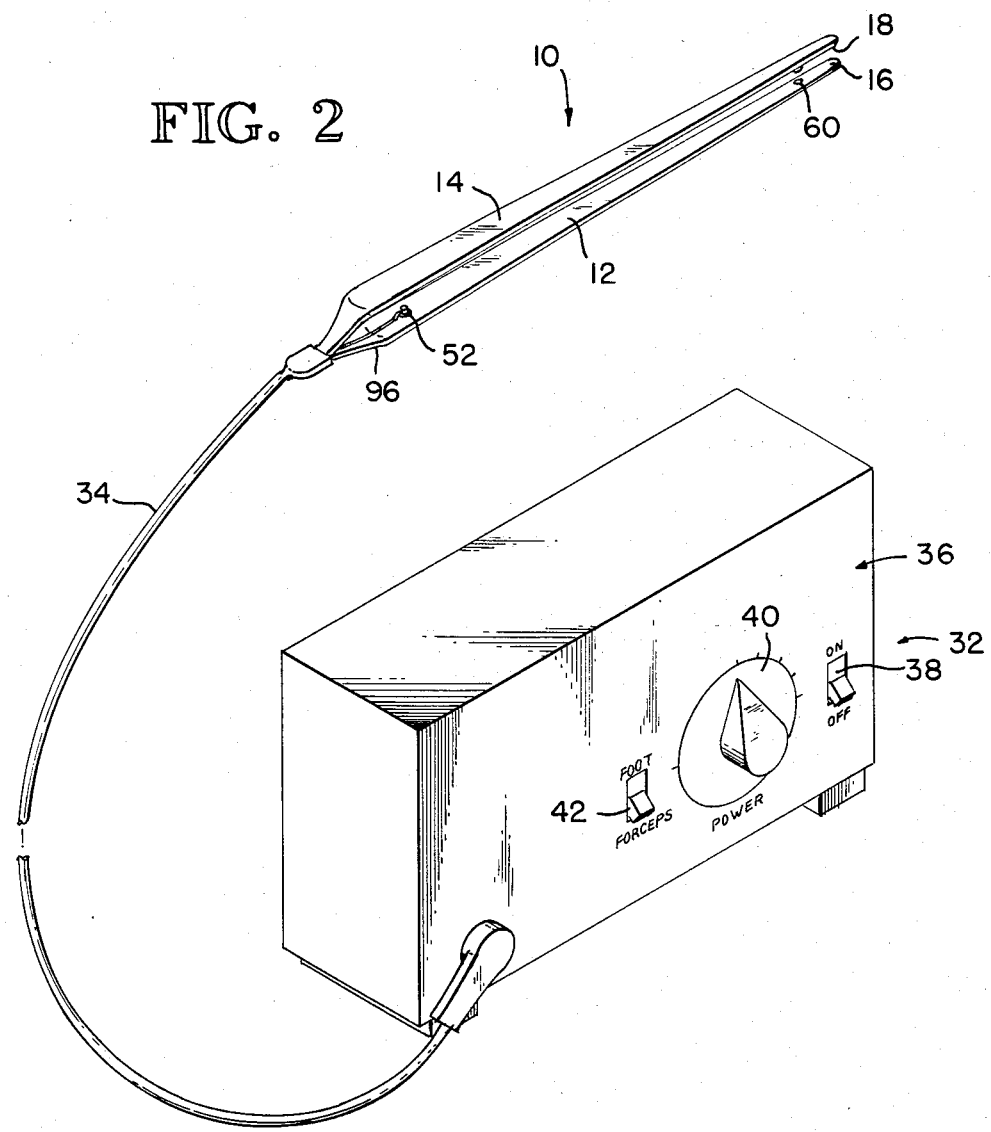

NON-STICKING ELECTROCAUTERY SYSTEM AND FORCEPS

DESCRIPTION

1. Technical Field

This invention relates to the field of electrosurgery, and more specifically, to an electrocoagulation electrodes having heat transfer characteristics which eliminate undesirable adhesion of tissue to the electrode.

2. Background Art

Application of heat to control bleeding dates to ancient times. Since the turn of the century, radio frequency-induced heat has been used for surgical purposes. Early radio frequency devices used spark gap generators for excitation of highly damped, sinusoidal, radio frequency waves and vacuum tube oscillators for excitation of more or less steady state radio frequency waves. Since the 1930's, conventional wisdom has maintained that highly damped wave forms were best for cutting operations. Various blends of cutting and coagulation wave forms inevitably evolved, leading to the relative level of coagulation being specified by the "crest factor" of the electrosurgical wave form. The "crest factor" is defined as the ratio of peak voltage to RMS voltage.

Clearly, with a higher crest factor and hence higher peak voltage, it is easier to draw a spark from an electrode to tissue. Many surgeons have advocated and taught this means of controlling discrete bleeders, resulting in its widespread use today. By using a spark as the conveyor of heat producing energy to the tissue, sticking of the electrode is obviated, since no direct touching of the tissue occurs. Unfortunately, the use of spark energy results in unpredictable damage to the tissue bed.

A sparking or "fulguration" electrosurgical device is generally "monopolar" in the sense that the electrical current proceeds from a smaller "active" electrode to the tissue, through the tissue to a "dispersive electrode," also known as a "patient plate" or "indifferent electrode," which completes a circuit with the electric generator. The dispersive electrode is large in its contact area (approximately 9 $cm^2$ for each 100 watts of electrical power delivered). Because of its broad exposure area, dissipation-induced temperature rise is insignificant, so the dispersive electrode does not produce cutting and coagulation. In contrast, the active electrode is typically of a dimension of the order of 1 mm, and thus concentrates the dissipated electrical current to a highly confined region with rapid rise in tissue temperature. One of the hazards frequently associated with the use of monopolar electrosurgery is the inadvertent reduction of area at the dispersive electrode which has resulted, in some cases, in severe burns to the patient's buttocks or legs.

Neuromuscular stimulation is highly diminished about 20,000 Hz. Thus, in order to avoid muscular stimulation, frequencies of between 0.5 MHz and 3 MHz are typically used in electrosurgery. However, rectification of the RF wave form can take place at the junction of the active electrode and the tissue, resulting in low-frequency generation. The propagation of these low-frequency currents can be substantially eliminated by using high-frequency band-pass filters, normally consisting of series capacitors.

Instead of using a monopolar system having a small active and a large dispersive electrode, a bipolar system having two small, closely spaced electrodes can be used. The electrodes are connected to opposite polarities of an RF generator and are spaced apart from each other so they can induce electrical current in tissue proximate to their contacting surfaces. Such induction of current in a locally defined area can lead to elevated temperature and resulting coagulation. Such devices have been used for many years, with the earliest known device being shown in U.S. Pat. No. 164,184, to Kidder. In the Kidder device, a pair of spirally wound conductors form a helical coagulator. A similar helically wound bipolar coagulator is disclosed in U.S. Pat. No. 1,983,669, issued to Kimble. Various monopolar and bipolar electrosurgical and electrocautery devices, and techniques for their use, are described in *Therapeutic Medical Devices*, Prentice-Hall (1982), Webster, Cook, eds., Chapter 10 by Knickerbocker et al.

Electrocautery procedures are sometimes implemented with forceps and hemostats which are routinely used as purely mechanical pickup, holding, and cautery devices in surgery. Frequently, a surgeon will "buzz" a hemostat which is grasping a blood vessel with a spark of monopolar coagulating radio frequency. The electrical current propagates through the metal arms of the hemostat to the tissue trapped in the jaws. The current continues to propagate through the vessel, eventually returning to the dispersive electrode. Forceps or surgical tweezers are commercially available with either monopolar or bipolar electrification. In monopolar versions, the radio frequency current propagates through the metal arms to the trapped or grasped vessel into the tissue substrate, returning to the dispersive electrode. In bipolar coagulation, the dispersive electrode is unnecessary to complete the circuit since each electrode of the bipolar applicator provides the return path for the other. By removing the potentially hazardous dispersive electrode, bipolar coagulation has gained acceptance as a safer modality in surgery. Perhaps more significant is the fact that bipolar coagulation produces a shallower and more predictable depth of coagulation necrosis. The reason for this is that the current path is tightly confined to the tissue proximate the two active elements touching the tissue. The current does not wander about as it travels downward into the tissue substrate, seeking out the dispersive electrode placed as much as 1.5 meters distal.

In its current commercial embodiment, the arms of monopolar and bipolar coagulation forceps frequently adhere to the tissue which they are coagulating. When this happens, it is necessary to tug on the vessel to separate the forceps which have been welded to the tissue. When the forceps finally separate from the tissue, bleeding frequently reoccurs at the same location and some tissue mass normally remains on the active surface of the forceps. This requires frequent cleaning or excessive generator voltage to spark through debris. In commercial units, high crest factor wave forms cause sparking, charring of tissue, and excessive tissue damage. These limitations on safety, efficacy, and convenience slowed the acceptance of this modality.

Electrosurgery and electrocautery electrodes (either active monopolar or bipolar) are normally fabricated from materials such as stainless steel or titanium, which, because of their surface hardness and inert properties, are frequently used to fabricate surgical instruments.

DISCLOSURE OF INVENTION

The primary object of the invention is to provide a non-sparking electrocautery system having electrodes that will not stick to the cauterized tissue.

It is another object of the invention to provide an RF signal generator for an electrocautery system having a relatively low output impedance.

It is still another object of the invention to provide a non-stick electrocautery system that does not electromagnetically interfere with other electronic equipment typically found in an operating room.

It is a further object of the invention to provide a bipolar electrocautery forceps that can be used in a nonpinching mode to cauterize vascularized tissues and vessels buried in tissue.

It is a still further object of the invention to provide a bilateral electrocautery forceps that automatically causes RF energy to be applied to the forceps as the forceps is closed.

These and other objects of the invention are provided by an electrocautery system having an RF signal generator connected between a pair of electrodes which are in contact with tissue. At least one of the electrodes is active so that it cauterizes tissue with which it is in contact. Each active electrode has a thermal conductivity that is high enough to maintain the surface of the electrode in contact with the tissue at a relatively low temperature to prevent the tissue from adhering to the electrode surface. At the same time, the tissue away from the electrode is raised to a temperature sufficient to produce coagulation. The electrodes are preferably formed by bipolar electrocautery forceps having a pair of electrically isolated forceps arms between which the RF signal is applied. The forceps arms terminate in respective, closely spaced jaws which apply the RF signal to the tissue between the jaws. The high thermal conductivity of the forceps arms removes heat from the jaws at a rate sufficient to maintain their surfaces that contact the tissue at a temperature below which tissue would adhere to the jaws. In practice, the surfaces of the jaws contacting the tissue will be maintained at a temperature of less than 96° C., while sufficient RF current is applied to the tissue to produce coagulation within an acceptable period of time. These requirements can be achieved by forceps having arms with thermal conductivities of greater than about 60 mW/mm°C. The forceps can be used in a pincer mode, in which a vessel is grasped between the jaws of the forceps arms. Alternatively, an insulating stop projecting from one arm toward the other prevents the forceps arms from contacting each other, thus allowing the forceps arms to be closed to the stop and then moved along in contact with vascularized tissue. The RF generator powering the forceps has a relatively low output impedance on the order of about 70 ohms. However, the output impedance is preferably contoured so that the tissue receives a relatively constant power as the tissue impedance varies. The forceps preferably includes an internal switch that automatically energizes the RF signal generator as the forceps is closed. This switch can be implemented by a contact mounted on at least one of the forceps arms and projecting inwardly so that it makes contact with the other forceps arm as the forceps is closed.

DESCRIPTION OF THE DRAWINGS

FIG. 2 is an isometric view of the electrocautery system incorporating a bipolar forceps embodiment of the invention.

BEST MODE FOR CARRYING OUT THE INVENTION

The primary reason for adherence of tissue to the contacting surface of electrocautery electrodes is excessive temperature rise at the junction of the tissue to the electrode surface. The tissue is thus excessively dessicated and tissue proteins are bound to the surface of the metal. It is worthy to note that excellent coagulation of tissue proteins, including blood protein, occurs in the range of 50°-80° C., substantially below the boiling point of water. Thus, if the temperature can be confined to a range below rapid boil-off of water, but above rapid coagulation, non-stick coagulation can occur.

Figure 1:
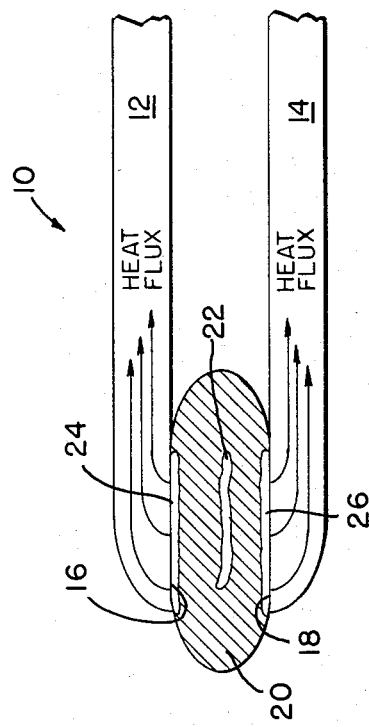
FIG. 1 is a schematic showing the manner in which a bilateral forceps embodiment of the invention is used to cauterize a vessel in a manner that prevents the vessel from sticking to the forceps.

It is possible to design electrocautery electrodes which contain distal temperature sensors which provide a servo control of the temperature to avoid excessive heating, but this greatly increases the cost to manufacture. Moreover, temperature regulation in this manner may adversely reduce the rate at which desirable coagulation can occur. A more advantageous technique is to design the electrode so that the interface region between the metal surface and the tissue is rapidly cooled. This is accomplished by forming the electrode with metals or metal alloys having very large thermal conductivities. With reference to FIG. 1, a bilateral forceps 10 embodiment of the invention includes two arms 12,14 connected between a source of radio frequency (RF) energy. The arms 12,14 terminate in respective jaws 16,18, which are shown pinching a blood vessel 20. RF current flowing between the jaws 16,18 is dissipated in the vessel 20, thereby producing heat for coagulating blood 22 in the interior of the vessel 20. The temperature of the vessel must be at least 50°-60° C. to provide coagulation, but in practice, the temperature is significantly higher. Thus, the temperature of the vessel 20 contacting the jaws 16,18 is usually high enough to produce rapid evaporation of entrained water. As a result, the vessel 20, and vascularized tissues in other applications, frequently stick to the jaws 16,18. It has not been heretofore recognized that adequate heating of the vessel 20 for coagulation can occur even if the temperature of the vessel 20 adjacent the jaws 16,18 is relatively low. Moreover, it has not been appreciated that a relatively thin interface zone 24,26 adjacent each jaw 16,18, respectively, can be maintained at this relatively low temperature by rapid removal of heat from the interface zones 24,26 through the arms 12,14 of the forceps 10. Removal of het generated in the interface zones 24,26 can be enhanced by the proper selection of material forming the forceps 10. Instead of choosing the normally used stainless steel or titanium, the material forming the forceps 10 is chosen for its high thermal conductivity. A high thermal conductivity allows the arms 12,14 to draw heat from the interface zones 24,26 at a faster rate, thus allowing a higher temperature at the interior of the vessel 20 without causing excessive temperatures in the interface zones 24,26. In conventionally used metals of lower conductivity, a hot spot is normally formed in the vessel 20 as well as in the interface zones 24,26. When the forceps jaws 16,18 provide for rapid thermal evacuation of heat in the interface zones 24,26, a hot spot is left in the interior of the vessel 20, but the interface zones 24,26 are kept at a substantially lower temperature. This means that adequate power levels can be injected into the tissue to effect rapid coagulation, but the interface zones 24,26 adjacent to the metal jaws 16,18 are kept sufficiently cool to permit adhesion-free performance.

Titanium and stainless steel, conventionally used for extant, commercially available, bipolar forceps, are poor thermal conductors, although excellent in their mechanical and chemical properties. The thermal conductivity of stainless steel (SS 316) is 0.16 W/cm°K. and titanium is 0.20 W/cm°K. Choosing a material for a surgical instrument for its thermal properties rather than for its mechanical and chemical properties is thus a departure from conventional wisdom. However, certain alloys possess high thermal conductivity and adequate mechanical properties as well. Their chemical inertness can be enhanced by using thin metallic coatings which offer little resistance to the flow of heat, but provide excellent chemical barriers to tissue fluids. Two alloys which offer excellent combinations of electrical conductivity, thermal conductivity, and mechanical stiffness are 70% silver/30% copper and 0.2–0.6% beryllium/about 97% copper/1.4–2.3% nickel. The thermal conductivity of 70Ag/30Cu is approximately 3.2 W/cm°K., and 0.2–0.6% Be/97% Cu/1.4–2.3% Ni is approximately 1.9 W/cm°K. The copper provides the high thermal conductivity, while the beryllium and nickel improve the mechanical properties of copper. Cobalt can also often be used as a substitute for nickel. These materials possess thermal conductivities which are more than nine times better than stainless steel or titanium. Other alloys have similar combinations of useful physical properties.

In order to provide for the non-stick operation of the non-stick electrocoagulator, there should be a substantial difference in the evaporation rate of blood entrained in the interior of the vessel versus that which is entrained in the periphery adjacent to the electrode to which sticking is to be avoided. Establishing an evaporation rate at the periphery next to the electrode which is one-half that of the interior is possible by cooling the interface zones 24, 26 to a temperature approximately 18° C. below that of the 96° C. boiling point of blood. Because of the large heat of vaporization, vascularized tissue temperature is clamped at about 96° C. until essentially all of the water is evaporated in the local region. Thus, with rapid coagulation such as is desirable in surgical coagulation, the interior zone is rapidly heated to a clamped temperature of 96° C. Establishing a cooled interface zone 24,26 of 0.1 mm does not impair coagulation effectiveness, but does provide a thin, moist boundary layer which conveniently releases the tissue from the jaws 16,18. Establishment of an 18° C. temperature drop across a 0.05 mm layer of tissue implies, given a tissue thermal conductivity of 0.675 mW/mm°C., a heat flux of 243 mW/mm$^2$. In order to maintain the boundary layer at 78° C. (96° C.-18° C.), it is necessary to not only evacuate the thermal energy transported from the interior region, but it is also necessary to evacuate that energy deposited by resistance heating within the interface zones 24,26. Rapid tissue coagulation requires a dissipation loss of about 3 W/mm$^3$ from resistance heating. In each 0.5 mm. thick interface zone 24,26, each 1 mm$^2$ of surface area will, under typical operating conditions, generate about 0.15 W of power which needs to be evacuated. Thus, in addition to the interior heat flux of approximately 243 mW, an additional 150 mW, or a total of 393 mW, needs to be evacuated from each mm$^2$ of the contact surface of each interface zone 24,26.

Heat from the interface zones 24,26 will propagate through the jaws 16,18 and up to the arms 12,14 of the forceps 10. There will be some radiation and convection cooling along the arms 12,14. To obtain an approximate estimate of the length of arms 12,14 required to participate in the heat transfer process, it is worthwhile to consider the heat capacity of typical metals at body temperature. For most metals, the heat capacity at body temperature is equal to approximately 3.0 mJ/mm$^3$°C. For a typical coagulation interval of 1 second, a total energy of 393 mJ must be transferred through each mm$^2$ of the tissue-contacting surface of each jaw 16,18 in order to adequately cool the tissue in the interface zone 24,26. For purposes of convenient calculation, it is assumed that the arms 12,14 are not tapered and that each square mm of the jaws 16,18 are contiguous with an equivalent cross-sectional area of the arms 12,14 for heat transport purposes. Given a boundary layer temperature of 78° C. and a background body temperature of 38° C., an approximate average temperature rise for the hot zone of the forceps will be at the midpoint of the two temperature extremes, or 58° C., representing an average temperature increase of 20° C. Thus the average energy absorption of the metal is 20 times 3 mJ per mm$^3$, or 60 mJ/mm$^3$. Thus, in a 1 second application of RF energy, the number of mm$^3$ required for heat absorption in the metal, given these conditions, is 393 mJ/60 MJ=6.55 mm$^3$, or a length of approximately 6.5 mm along the arms 12,14 of the forceps 10. The temperature gradient is thus 40° C./6.5 mm, 6.2° C./mm. In order to transport 393 mW per square mm of cross-sectional area with such a temperature gradient, a thermal conductivity of (393 mW/mm$^2$)/6.2° C./mm)=63.4 mW/mm°C. is required. Such a value is about three times that of titanium and about four times that of stainless steel. This value is easily exceeded with copper (approx. 390 mW/mm°C.) or with high-strength silver-copper alloys or even higher strength beryllium-nickel-cobalt-copper alloys.

A preferred embodiment of the forceps 10, as illustrated in FIG. 2, includes an electrically insulating hinge joining the arms 12,14. The arms 12,14, made from a material having a suitably high thermal conductivity, such as 2% beryllium/98% copper plated with nickel to a thickness of 10 microns to provide chemical inertness and surface hardening. The forceps 10 are connected to an RF generator 32 through a shielded cable 34. The shielded cable 34 will normally be electrically connected to the grounded chassis of the RF generator 32 and insulated on its outer circumference with dielectric material. As a result, the cable does not emit electromagnetic radiation to any appreciable degree. Moreover, the relatively low peak voltages between the arms 12,14 of the forceps 10 and low bandwidth inherent in low crest factor operation and the use of an RF generator having a low output impedance further reduces electromagnetic interference. The RF generator 32 has a front panel 36 containing an on/off switch 38, a rotatable power control potentiometer 40, and a mode switch 42 for making RF generator 32 actuatable by either a foot switch or a switch built into the forceps 10. The forceps switch includes a contact 52 projecting from one arm 12 toward the other arm 14. Mechanical displacement of the arms 12,14 causes the contact 52 to touch arm 14, thereby triggering the radio frequency generator 32 through respective wires (shown hereinafter). Thus the surgeon automatically activates the RF generator 32 when the forceps 10 are squeezed beyond a certain preset position. This option can be defeated by actuating the switch 42 for those circumstances wherein the forceps 10 are needed for purely nonelectrical grasping purposes. In contrast to this internal switch, conventional bipolar forceps are activated by means of a foot switch placed near the surgeon's foot. During an actual procedure, the surgeon frequently has difficulty groping around with his foot to find the pedal and then makes an effort to sustain his balance while pressing same. The inventive forceps 10 can, of course, be used in this conventional mode when the switch 42 is moved to its downward position.

Although the normal mode of operation of the forceps 10 is the "pincer mode" shown in FIG. 1, in which a vessel 20 is grasped in the jaws 16,18 prior to coagulation, an optional feature of the forceps 10 is the incorporation of an insulating stop 60 (FIG. 2) which prevents complete closure of the forceps 10 in the absence of intervening tissue. Hence, metal-to-metal contact is not possible, thereby eliminating microwelding of the metal jaws 16,18 and carbonization buildup from microscopic residual debris. Incorporation of the insulating stop 60 provides a very important operating convenience consisting of end-on-spot-coagulation. In this mode of operation, the surgeon closes the forceps 10 as far as they can go, i.e., up to the point of pressure on the insulating stop 60. Electrical activation of the forceps in this closed position projects an electrical field in the space in front of and to the sides of the forceps 10 which can excite currents in tissue in contact with the forceps jaws 16,18. By using a stop 60 of dimension much less than 1 mm, the forceps 10 confine their spot coagulation to a very small region of tissue space and yet provide in one and the same instrument the ability to grasp small vessels in pincer fashion. When the forceps 10 are closed to the insulating stop 60 and electrically energized, they can be moved along tissue in a linear path, depositing a linear zone of coagulation. This is useful for tracking a given vessel to assure coagulation and/or obliteration, or as a precoagulation to incision. The ability to deposit spot coagulation is a great surgical advantage since it causes very little tissue damage in comparison to conventional fulgurating methods, and yet provides spot coagulation without sticking to tissue. In those episodes of bleeding wherein the vessels are buried in the tissue substrate, the spot coagulation mode is very useful since it is impossible, without further dissection, to grasp the vessel in the pincer mode. This non-stick touch method is of further advantage in comparison to the monopolar fulguration method in that vessel compression results from mechanical contact and pressure assists hemostasis by mechanical tamponade and endothelium-to-endothelium contact prior to cautery.

The insulating stop 60, as illustrated in FIG. 2, may consist of a plastic rivet chosen of proper thickness. Alternatively, it may be formed simply as a result of using an insulating plastic coating over the arms 12,14 and a portion of the jaws 16,18. This plastic coating does not cover the portion of the forceps designed for electrical conduction to tissue. An insulating coating provides electrical insulation for the surgeon such that inter-arm currents through the surgeon's hands are impeded even without surgical gloves. Furthermore, electrical conduction through electrolyte residue or puddles or adjacent tissue are impeded by such insulating coating. The coating is preferably made from high-temperature, high-slip plastic.

Figure 3:
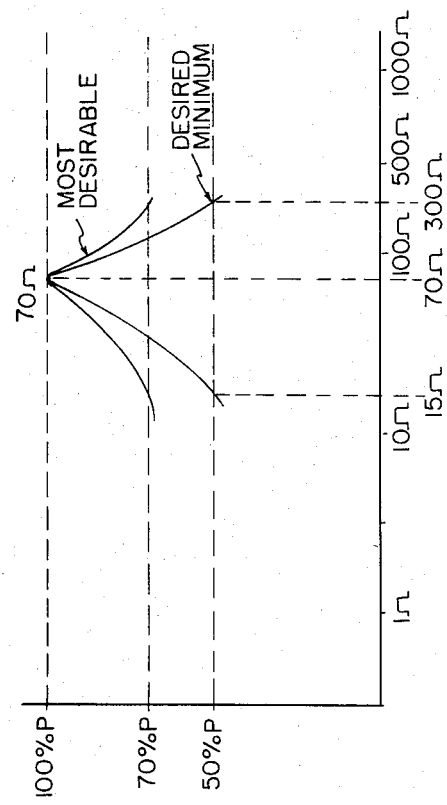
FIG. 3 is a graph showing the power delivered to cauterize the tissue by the RF signal generator as a function of tissue impedance.

As mentioned above, many conventional electrocautery electrodes and their associated radio frequency electrical generators use high crest factor wave forms to energize the electrodes. This results in production of sparks, which tends to produce excessive tissue damage. Sparking produces high peak thermal hot spots in time frames of less than 1 millisecond. Thus, excessive local heating can occur before even electrodes having a high thermal conductivity can drain it away. However, it is possible to deliver adequate coagulation power without using a spark-producing, high crest factor wave form. It is also possible to supply electrical power sufficient for coagulation of large blood-wetted or saline-wetted tissue areas without using high voltage levels, provided the RF generator 36 is designed to deliver a relatively uniform amount of power into load impedances varying from 15 ohms to 300 ohms. The preferred levels of power applied to the tissue through the forceps 10 as a function of tissue impedance is shown in FIG. 3. Note that the power applied to the tissue peaks at a tissue impedance of about 70 ohms, but that the increase and roll-off of power are less than would be expected for a constant RF generator output impedance. A power profile, such as illustrated in FIG. 3, can be easily implemented with a variety of circuits known to one skilled in the art, such as a negative feedback circuit in conjunction with an RF power detector. Even an RF generator having a constant output impedance will exceed the "desired minimum" impedance profile.

A relatively flat power profile is important in supporting coagulation in electrically conductive tissue u having widely varying impedance levels. This aids the surgeon by providing for effective coagulation in a wide variety of coagulation episodes during the course of a surgical procedure without readjusting the generator power potentiometer 40. By using a generator output impedance which is abnormally low compared to the standard, commercially available units, it is possible to provide more universal control of bleeding. Furthermore, the need for increasing open-circuit voltage in order to provide adequate power into a low value of load impedance is eliminated. In fact, an open-circuit voltage of 40 volts RMS and 60 volts peak is adequate to provide consistent coagulation with forceps 10 whose jaws 16,18 are not contaminated by insulating dessicated blood and tissue, provided the generator output impedance versus power complies with FIG. 3. This contrasts to peak voltage levels observed in conventional fulgurating generators of more than 500 volts. As a result, sparking is eliminated, thereby eliminating hot spots. Furthermore, the high voltage used in fulgurating generators or high crest factor generators causes excessive radiation interference to operating room monitors, which is also greatly reduced by maintaining peak voltages of less than 70 volts and by reducing the electrical bandwidth inherent in larger crest factor designs. Thus, in addition to a departure from conventional wisdom in the choice of metal for the arms 16,18, the inventive electrocautery system departs from conventional design by reducing the crest factor to below 2 and the peak voltage below 70 volts. Both of these departures from conventional wisdom are possible by using active electrodes, which will not build up insulating debris, and using an RF generator having a relatively low voltage output and a relatively low output impedance capable of more than 50% power into a load of 15 ohms. As a result of the much improved efficiency in coagulation made possible by maintenance of electrically clean forceps jaws 16,18 and by broad, relatively flat impedance contouring into the very low impedance regime (15 ohms), it is possible to limit the available power to the surgeon to 15 watts (RMS).

Figure 4:
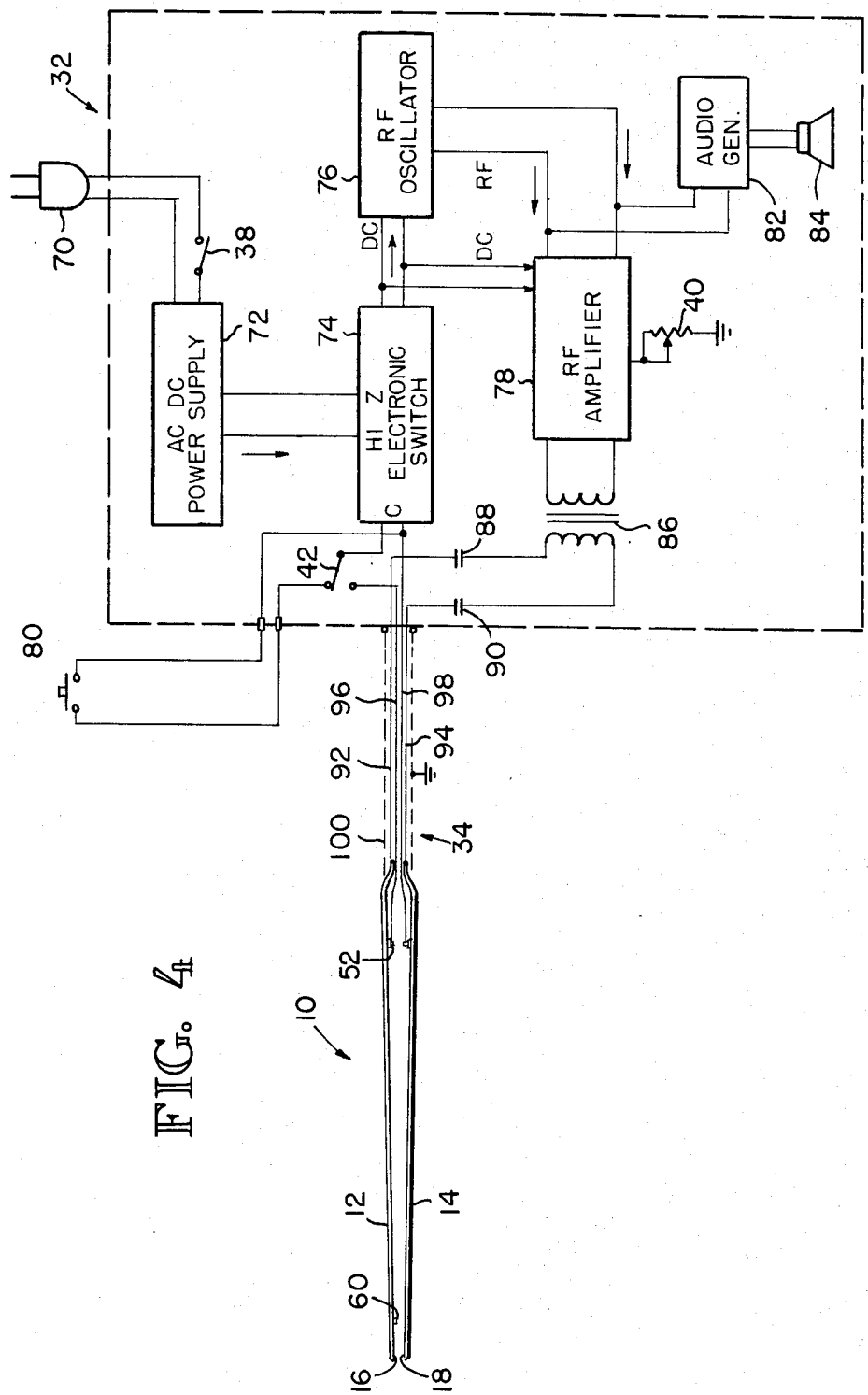
FIG. 4 is a block diagram of the RF signal generator applying RF power to a bipolar forceps.

One embodiment of the RF generator 32 is illustrated in FIG. 4. The generator 32 receives AC power from a conventional wall outlet through plug 70 connected to a conventional DC power supply 72 through the on/off switch 38. The power supply 72 applies DC power to a conventional electronic switch 74 having a pair of control inputs that selectively switch the DC output from power supply 72 to a conventional RF oscillator 76 and a conventional RF amplifier 78. One of the control inputs to the electronic switch 74 is connected to one contact of a conventional foot switch 80 and to one arm 14 of the forceps 10. The remaining control input to switch 74 is connected to either the other contact of foot switch 80 or the other contact 52 of the forceps 10 through the mode switch 42. This, actuating the mode switch 42 in either position makes the electronic switch 74 controlled by either the foot switch 80 or the contact 52 in the forceps 10. In either case, when the switch 74 applies power to the RF oscillator 76 and RF amplifier 78, the oscillator 76 generates an RF signal of appropriate frequency. This RF signal is boosted by the RF amplifier 78 by an amount controlled by the power control potentiometer 40. The power control potentiometer 40 may be continuously adjustable or it may have fixed positions or detents so that only a number of predetermined power levels may be selected. The output of the RF oscillator 76 is also applied to a conventional audio generator 82 driving an audio speaker 84. Basically, the audio generator detects the presence of the RF signal from oscillator 76 through, for example, use of a diode. The detected RF signal is then used to apply power to an audio oscillator and power amplifier which drives speaker 84. Thus, the RF generator 36 provides an audible indication that power is being applied to the forceps 10.

The output of the RF amplifier 78 is connected to the primary of an RF transformer 86 having its secondary connected through capacitors 88,90 to respective arms 12,14 of the forceps 10. The capacitors 88,90 implement a high-pass filter to prevent the possibility of DC or low-frequency AC signals (such as the 60 Hz power signal) from being applied to the patient's body through the forceps 10. As mentioned above, the shielded cable 34 contains a pair of wires 92,94 connecting the RF generator 32 to the arms 12,14, respectively, and a second pair of wires 96,98 connecting the contact 52 and the arm 14, respectively, to the generator 32. The wires 92-98 are all surrounded by a flexible metal shield 100 to reduce the possibility of electromagnetic interference.

In operation, the surgeon actuates the on/off switch 38 to apply power to the system. After selecting the desired operating mode with mode switch 42, the surgeon then selects the appropriate cauterizing level with power control potentiometer 40. The surgeon may then place a vessel between the jaws 16,18 of the forceps 10, and power is applied to the arms 12,14 of the forceps 10, either because of touching between the contact 52 and arm 14 when the jaws 16,18 are closed or because of actuation of the foot switch 80. Alternatively, the arms 12,14 may be pressed toward each other to the limit of the stop 60, while RF power is continuously applied to the forceps 10. The ends of the arms 12,14 can then be placed on or drawn along vascularized tissue or a vessel to provide coagulation. The high thermal conductivity of the arms 12,14 draws sufficient heat away from the tissue or vessel in the interface zone adjacent the jaw 16,18 to maintain the temperature of the interface tissue or vessel below about 80° C. The temperature is maintained at this level even though the temperature in the vessel or tissue away from the jaws 16,18 is significantly higher. As a result, fast and thorough coagulation of the vessel or tissue occurs without the tendency of the jaws 16,18 to stick the vessel or tissue. Moreover, the use of a relatively low RF voltage level and low crest factor wave forms provides spark-free operation with the attendant advantages of reduced tissue damage and reduced electromagnetic interference. The inventive electrocautery system is most advantageously employed in its bipolar format. Thus, the system is primarily discussed with reference to the bipolar forceps system shown herein. However, the inventive concepts can also be applied to monopolar electrocautery systems.

I claim:

1. A non-sticking electrocautery forceps adapted for use with an RF signal generator producing an RF signal, said forceps comprising a pair of electrically conductive forceps arms electrically isolated from each other between which said RF signal is adapted to be applied, said forceps arms terminating in respective, closely spaced jaws, each having a tissue contact surface through which said RF signal is adapted to be applied to tissue positioned in contact with said jaws, each of said forceps arms having a volume of heat-absorbing material of at least about 6.5 mm$^3$ for each mm$^2$ area of said tissue contact surface, said heat-absorbing material having a thermal conductivity of at least 60 mW/mm°C. such that said heat-absorbing material is capable of both transferring heat at a sufficient rate and absorbing heat in a sufficient quantity to maintain said tissue contact surface at a temperature low enough to prevent tissue from adhering to said tissue contact surface while said forceps delivers power to said tissue to raise the temperature of said tissue to a level sufficient to produce coagulation, said jaws having a relatively hard protective coating applied thereto, thereby chemically isolating tissue from said heat-absorbing material and mechanically protecting said jaws.

2. The electrocautery forceps of claim 1 wherein said forceps further includes an electrically insulating stop projecting from one forceps arm to the other at a location spaced apart from the jaws of said forceps arms to prevent said tissue contact surfaces from contacting each other responsive to compressive forces drawing said forceps arms toward each other.

3. The electrocautery forceps of claim 1 wherein the major portion of said forceps, with the exception of said tissue contact surfaces, is coated with an insulating material.

4. The electrocautery forceps of claim 1 wherein substantially all of each forceps arm is of a material having a thermal conductivity of at least 60 mW/mm°C.

5. An electrocautery system comprising:

an RF signal generator producing an RF signal between a pair of terminals; and an electrocautery forceps having a pair of electrically conductive forceps arms electrically isolated from each other and connected to respective terminals of said RF signal generator, said forceps arms terminating in respective, closely spaced jaws, each having a tissue contact surface through which said RF signal is applied to tissue positioned in contact with said jaws, each of said forceps arms having a volume of heat-absorbing material of at least about 6.5 mm$^3$ for each mm$^2$ area of said tissue contact surface, said heat-absorbing material having a thermal conductivity of at least 60 mW/mm°C. such that said heat-absorbing material is capable of both transferring heat at a sufficient rate and absorbing heat in a sufficient quantity to maintain said tissue contact surface at a temperature low enough to prevent tissue from adhering to said tissue contact surface while said forceps delivers power to said tissue to raise the temperature of said tissue to a level sufficient to produce coagulation, said jaws having a relatively hard protective coating applied thereto, thereby chemically isolating tissue from said heat-absorbing material and mechanically protecting said jaws.

6. The electrocautery system of claim 5 wherein said RF signal generator is externally triggered through a trigger input to apply said RF signal to said forceps, and wherein said forceps includes an RF switch that closes as said arms move toward each other a predetermined distance, said switch being connected to the trigger input of said RF signal generator so that said signal generator automatically applies said RF signal to said forceps as the arms of said forceps are closed.

7. The electrocautery system of claim 6 wherein said switch includes one contact member projecting from one of said forceps arms to the other, said contact member making contact with the other of said forceps arms as forceps arms are closed toward each other.

8. The electrocautery system of claim 1 wherein said RF generator has an output impedance of about 70 ohms.

9. The electrocautery system of claim 5 wherein said RF generator further includes output circuit means for adjusting the output impedance of said RF generator as a function of the impedance of tissue between said tissue contact surfaces so that the power applied to said tissue peaks at a predetermined tissue impedance but increases toward and decreases away from peak.

10. The electrocautery system of claim 5 wherein said RF generator produces an unloaded peak output of less than about 70 volts.

* * * * *